(12) United States Patent
Lee et al.

(10) Patent No.: US 9,658,147 B2
(45) Date of Patent: May 23, 2017

(54) APPARATUS FOR MEASURING SATURATED HYDRAULIC CONDUCTIVITY OF UNSATURATED POROUS MEDIA

(71) Applicant: Korea Institute of Geoscience and Mineral Resources, Daejeon (KR)

(72) Inventors: Bong-Joo Lee, Daejeon (KR); Ji-Hoon Lee, Daejeon (KR)

(73) Assignee: KOREA INSTITUTE OF GEOSCIENCE AND MINERAL RESOURCES, Daejeon (KR)

( * ) Notice: Subject to any disclaimer, the term of this patent is extended or adjusted under 35 U.S.C. 154(b) by 48 days.

(21) Appl. No.: 14/850,291

(22) Filed: Sep. 10, 2015

(65) Prior Publication Data
US 2016/0076987 A1    Mar. 17, 2016

(30) Foreign Application Priority Data
Sep. 11, 2014    (KR) .............................. 2014-0120403

(51) Int. Cl.
*G01N 15/08*    (2006.01)
*E02D 1/00*    (2006.01)

(52) U.S. Cl.
CPC ........... *G01N 15/0826* (2013.01); *E02D 1/00* (2013.01)

(58) Field of Classification Search
CPC .............................. G01N 14/0826; E02D 1/00
See application file for complete search history.

(56) References Cited

U.S. PATENT DOCUMENTS

| | | | | |
|---|---|---|---|---|
| 2002/0095984 A1* | 7/2002 | Johnson | ............. | G01N 15/0826 73/152.05 |
| 2013/0340517 A1* | 12/2013 | Brown | ................... | G01N 33/24 73/152.05 |
| 2014/0116114 A1* | 5/2014 | Lee | ...................... | G01N 33/246 73/38 |

* cited by examiner

*Primary Examiner* — Hezron E Williams
*Assistant Examiner* — David Z Huang
(74) *Attorney, Agent, or Firm* — Dentons US LLP

(57) ABSTRACT

A apparatus for measuring saturated hydraulic conductivity of unsaturated porous media in an unsaturated zone of the earth. The measuring apparatus includes a cylinder member inserted into the porous media in a position in which the upper and lower ends of the cylinder member are open, a means for supplying a constant flow rate of water to the cylinder member, and a pressure measuring means for measuring the hydraulic head in response to water flowing into the cylinder member. The measuring apparatus can easily measure the vertical hydraulic conductivity of a foundation based on Darcy's Law in the field. It is possible to accurately measure the hydraulic conductivity of a sedimentary layer in the natural state and easily determine geological characteristics of the soil. It is possible to obtain very accurate information regarding the process of dispersion and movement of contaminants.

13 Claims, 7 Drawing Sheets

APPARATUS FOR MEASURING SATURATED HYDRAULIC CONDUCTIVITY OF UNSATURATED POROUS MEDIA

CROSS-REFERENCE TO RELATED APPLICATION

This application claims priority to Korean Patent Application No. KR 2014-0120403 filed on Sep. 11, 2014 and all the benefits accruing therefrom under 35 U.S.C. §119, the contents of which are incorporated by reference in their entirety.

BACKGROUND OF THE INVENTION

Field of the Invention

The present invention relates to an apparatus for measuring saturated hydraulic conductivity of unsaturated porous media in the field.

Description of the Related Art

Field measurements on the saturated hydraulic conductivity of porous media in an unsaturated zone are typically performed using a standpipe permeameter test, a method using aseepage meter and the hydraulic gradient between surface water and subterranean water, a slug test based on an instantaneous change in the water level, and an estimation method using an empirical formula based on particle size analysis of field-sampled porous media in a laboratory on field-sampled porous media. However, these methods have rather low objective reliability. For example, it is difficult to apply the standpipe permeameter and the method using a seepage meter and the hydraulic gradient between surface water and subterranean water in a place in which the interaction between surface water and subterranean water is active. Using the slug test to measure hydraulic conductivity, which is the lateral hydraulic conductivity of porous media to be measured, also requires vertical hydraulic conductivity to be measured therefrom. The estimation method using an empirical formula based on particle size analysis is accompanied with the sampling of porous media and post-test treatment, which consequently lowers the reliability of the test. A field saturated hydraulic conductivity measuring device recently developed and published (Korean Patent No. 10-1366057) shows a highly-reliable field assessment result. However, this device is designed to measure the hydraulic conductivity of surface water and the hydraulic conductivity of a lower portion of porous media.

A variety of methods are used for measuring the hydraulic conductivity of porous media in an unsaturated zone. Among these methods, a tension disk infiltration system, a Guelph infiltration system, a double-ring infiltration system, a velocity permeameter, and the like are generally used. However, each of these systems is also estimated as having low objective reliability in a field measurement of saturated hydraulic conductivity.

In the meantime, in order to measure the hydraulic conductivity using Darcy's Law, Darcian flux and a hydraulic gradient of a range to be measured is required. The hydraulic gradient can be obtained by measuring the amount of water supplied to a cylinder and a head difference of the range to be measured. The amount of water supplied to the cylinder in a steady state can be obtained using a metering pump, such as a peristaltic pump, or a Marriott's bottle (refer to Korean Patent No. 10-1252136). In order to visually measure the head difference in the range to be measured, the hydraulic head at the depth to be measured must be formed above the earth surface. When water having a certain pressure head is supplied along the earth surface within the cylinder, a head loss proportionally increases with increases in the depth of the portion of porous media to be measured. When the range to be measured is positioned deep, the hydraulic head at the corresponding depth is proportionally lowered. So, it is difficult to measure the hydraulic head from the earth surface. In order to overcome this, a method of minimizing the head loss of the pressure head by directly supplying water to the portion directly above the range to be measured without causing the water to flow through porous media at the corresponding depth is required.

The information disclosed in the Background of the Invention section is only for the enhancement of understanding of the background of the invention, and should not be taken as an acknowledgment or as any form of suggestion that this information forms a prior art that would already be known to a person skilled in the art.

RELATED ART DOCUMENTS

Patent Document 1: Korean Patent No. 10-1366057.
Patent Document 2: Korean Patent No. 10-1252136

SUMMARY OF THE INVENTION

Accordingly, the present invention has been made keeping in mind the above problems occurring in the related art, and the present invention is intended to propose a measuring apparatus able to measure the saturated hydraulic conductivity of unsaturated porous media using a cylinder member inserted into the porous media in a position in which the upper and lower ends of the cylinder member are open, a means for supplying a constant flow rate of water to the cylinder member, and a pressure measuring means for measuring the hydraulic head in response to water flowing into the cylinder member.

In order to achieve the above object, according to one aspect of the present invention, an apparatus for measuring saturated hydraulic conductivity of unsaturated porous media includes: a measuring tube disposed in a longitudinal direction such that a portion thereof is buried in a foundation, the measuring tube having a hollow portion therein extending in a top-bottom direction to contain a portion of porous media in an unsaturated zone of the foundation, the measuring tube including a first hydraulic head side connecting portion and a second hydraulic head side connecting portion on lower portions, the first hydraulic head side connecting portion being spaced apart from the second hydraulic head side connecting portion, and a first flow rate measuring-and-connecting portion disposed above and spaced apart from the first hydraulic head side connecting portion and the second hydraulic head side connecting portion; a Mariotte's bottle disposed on a ground, the Mariotte's bottle containing water therein with both ends thereof being closed, the Mariotte's bottle including a second flow rate measuring-and-connecting portion connected to the first flow rate measuring-and-connecting portion, wherein the Mariotte's bottle supplies a predetermined flow rate of water to the measuring tube through the flow rate measuring-and-connecting portion in response to air being supplied to an interior thereof; a first hydraulic head observation tube and a second hydraulic head observation tube respectively fixed to the first hydraulic head side connecting portion and the second hydraulic head side connecting portion and extending upward; and a flow rate measuring tube connecting the first flow rate measuring-and-connecting portion and the second flow rate measuring-and-connecting portion.

The apparatus may further include protective guides on an outer surface of the measuring tube respectively protruding from below the first hydraulic head side connecting portion, the second hydraulic head side connecting portion, and the first flow rate measuring-and-connecting portion to protect the first hydraulic head side connecting portion, the second hydraulic head side connecting portion, and the first flow rate measuring-and-connecting portion while the measuring tube is being buried in the foundation.

The protective guides may protrude in a wedge shape.

The apparatus may further include at least one gradient measuring device on an upper portion of the measuring tube.

The apparatus may further include: a gradient measuring plate on an upper portion of the measuring tube; and at least one gradient measuring device fixedly disposed on an upper surface of the gradient measuring plate.

The apparatus may further include a filter fixedly disposed on at least one of an inner side surface of the measuring tube on which the first flow rate measuring-and-connecting portion is disposed and an interior of the first flow rate measuring-and-connecting portion.

According to another aspect of the present invention, an apparatus for measuring saturated hydraulic conductivity of unsaturated porous media includes: a measuring tube including an inner tube and an outer tube forming a double tube structure, lower portions of the inner tube and the outer tube being connected to each other and forming a lower connecting portion, the measuring tube being disposed in a longitudinal direction such that a portion thereof is buried in a foundation, the measuring tube having a hollow portion therein extending in a top-bottom direction to contain a portion of porous media in an unsaturated zone of the foundation, the measuring tube further including a first hydraulic head side connecting portion and a second hydraulic head side connecting portion on lower portions between the inner tube and the outer tube, the first hydraulic head side connecting portion being spaced apart from the second hydraulic head side connecting portion, and a first flow rate measuring-and-connecting portion disposed above and spaced apart from the first hydraulic head side connecting portion and the second hydraulic head side connecting portion; a Mariotte's bottle disposed on a ground, the Mariotte's bottle containing water therein with both ends thereof being closed, the Mariotte's bottle including a second flow rate measuring-and-connecting portion connected to the first flow rate measuring-and-connecting portion, wherein the Mariotte's bottle supplies a predetermined flow rate of water to the measuring tube through the flow rate measuring-and-connecting portion in response to air being supplied to an interior thereof; a first hydraulic head observation tube and a second hydraulic head observation tube respectively fixed to the first hydraulic head side connecting portion and the second hydraulic head side connecting portion and extending upward; and a flow rate measuring tube connecting the first flow rate measuring-and-connecting portion and the second flow rate measuring-and-connecting portion.

The upper connecting portion may be disposed on an upper portion of the measuring tube to connect the upper portions of the inner tube and the outer tub. The upper connecting portion may have fixing holes fixedly holding the first hydraulic head observation tube and the second hydraulic head observation tube such that the first hydraulic head observation tube and the second hydraulic head observation tube are withdrawn upward.

The apparatus may further include at least one gradient measuring device on the upper connecting portion.

The outer tube may have a withdrawal hole through which the flow rate measuring tube is withdrawn.

The apparatus may further include a filter fixedly disposed on at least one of an inner side surface of the measuring tube on which the first flow rate measuring-and-connecting portion is disposed and an interior of the first flow rate measuring-and-connecting portion.

Any one of the above-described apparatuses may further include a packer disposed within the hollow portion of the measuring tube to selectively isolate an upper portion and a lower portion of the hollow portion from each other.

According to the technical solution as set forth above, it is possible to accurately measure the hydraulic conductivity of a sedimentary layer in the natural state, since the saturated hydraulic conductivity of the unbound sedimentary layer in an unsaturated zone can be easily measured in the field.

In particular, it is possible to continuously measure the hydraulic conductivity according to the depths of sedimentary layers. It is therefore possible to analyze the vertical permeability of a foundation structure, thereby obtaining very specific information regarding the process of dispersion and movement of contaminants.

In addition, the apparatus has a simple configuration and consequently can be easily disposed and managed. It is thereby possible to efficiently examine the foundation structure of a specific area.

Accordingly, it is possible to improve reliability and competitiveness in engineering work, geological surveys, subterranean water development, geological pollution prevention, and similar fields derivable therefrom.

BRIEF DESCRIPTION OF THE DRAWINGS

The above and other objects, features and advantages of the present invention will be more clearly understood from the following detailed description when taken in conjunction with the accompanying drawings, in which.

DETAILED DESCRIPTION OF THE PRESENTLY PREFERRED EMBODIMENTS

An apparatus for measuring hydraulic conductivity according to the present invention may have a variety of exemplary embodiments. Hereinafter, most exemplary embodiments thereof will be described with reference to the accompanying drawings.

Figure 1:
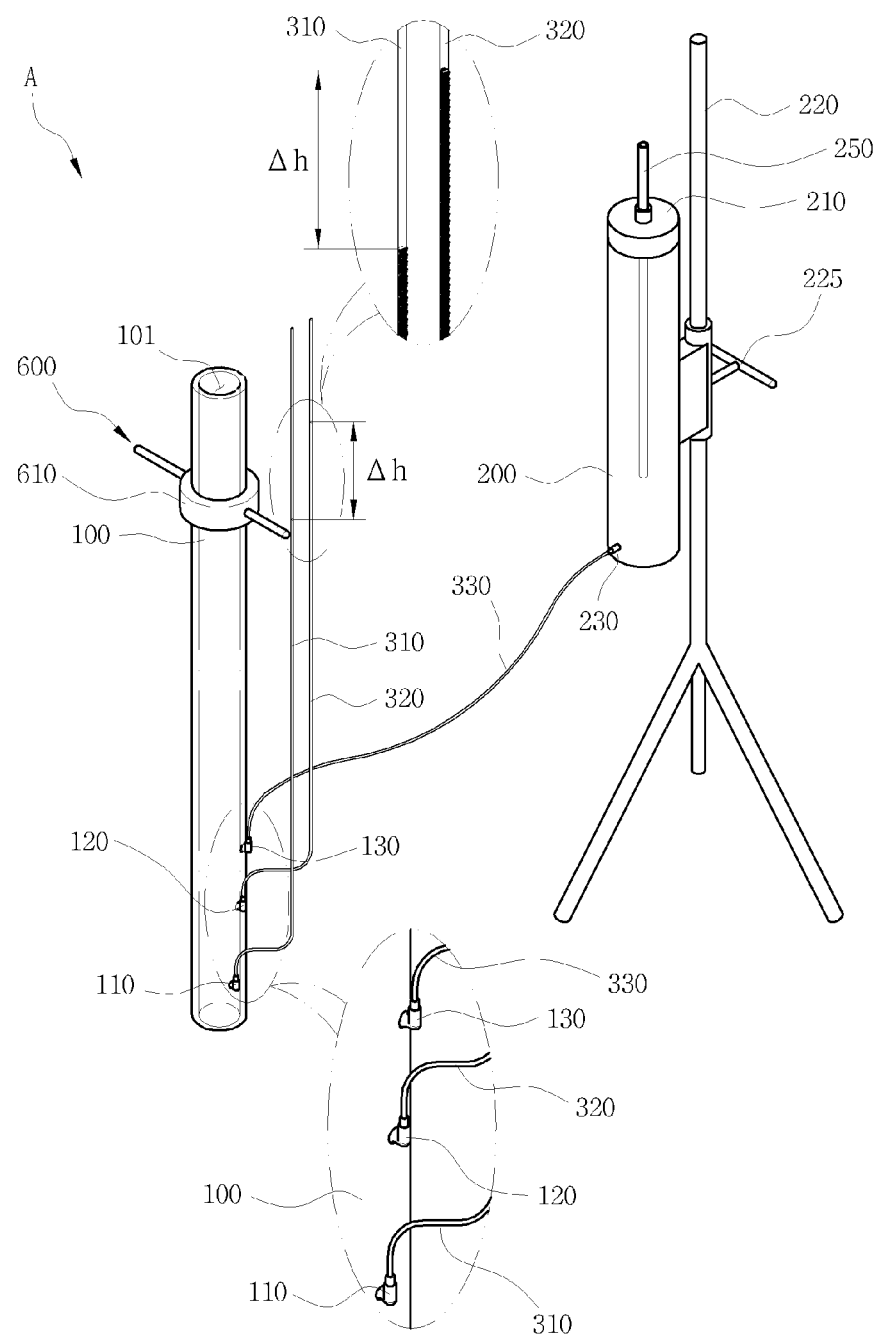
FIG. 1 is a configuration view illustrating an embodiment of an apparatus for measuring saturated hydraulic conductivity of unsaturated porous media according to the present invention.

FIG. 1 is a configuration view illustrating an exemplary embodiment of an apparatus for measuring saturated hydraulic conductivity of unsaturated porous media according to the present invention.

According to Darcy's Law, the flow rate of water passing through a column filled with a porous medium is proportional to the hydraulic gradient between two points within the column and the hydraulic conductivity of the medium. This explains that the hydraulic conductivity of the porous medium contained within the column can be accurately calculated when the flow rate of water passing through the column having a predetermined cross-sectional area and the difference in the hydraulic head between two points within the column are known.

Referring to FIG. 1, an apparatus A for measuring hydraulic conductivity includes a measuring tube 100, a Mariotte's bottle 200, a first hydraulic head observation tube 310, a second hydraulic head observation tube 320, and a flow rate measuring tube 330.

The measuring tube 100 is designed to measure hydraulic conductivity depending on the depth of a foundation, and has a hollow portion 101 extending through the length thereof in the top-bottom direction. The measuring tube 100 is disposed in the top-bottom direction, with a lower portion thereof being buried in the foundation. The measuring tube 100 contains therein porous media in an unsaturated zone of the foundation.

In addition, the measuring tube 100 has a first hydraulic head side connecting portion 110, a second hydraulic head side connecting portion 120, and a first flow rate measuring-and-connecting portion 130 on the lower portion.

A hydraulic gradient required by Darcy's Law can be obtained from the distance between the first hydraulic head side connecting portion 110 and the second hydraulic head side connecting portion 120 and the head difference Δh between the first hydraulic head observation tube 310 and the second hydraulic head observation tube 320.

For example, the first hydraulic head side connecting portion 110 is disposed on the lower end portion of the measuring tube 100, and the second hydraulic head side connecting portion 120 is spaced apart by a predetermined distance in the upward direction from the first hydraulic head side connecting portion 110. The first flow rate measuring-and-connecting portion 130 for measuring a flow rate between two points is disposed above the second hydraulic head side connecting portion 120.

In addition, the first hydraulic head observation tube 310 and the second hydraulic head observation tube 320 are respectively connected to the first hydraulic head side connecting portion 110 and the second hydraulic head side connecting portion 120 of the measuring tube 100 in order to measure the head difference Δh between the points.

Here, the first hydraulic head observation tube 310 and the second hydraulic head observation tube 320 are formed of a transparent material, allowing an observer to measure the head difference Δh, and extend upward along the measuring tube 100 above the surface of the earth.

Alternatively, pressure transducers may be disposed on the first hydraulic head observation tube 310 and the second hydraulic head observation tube 320 to measure the levels of water introduced to the tubes, thereby measuring the head difference Δh between two points.

In the meantime, water introduced through the first flow rate measuring-and-connecting portion 130 of the measuring tube 100 is discharged from the Mariotte's bottle 200 disposed on the surface of the earth.

The Mariotte's bottle 200 is an apparatus that continuously discharges a constant flow rate of water regardless of the level of water within the bottle.

The Mariotte's bottle 200 is formed as a hollow body with the upper end thereof being open, and has a second flow rate measuring-and-connecting portion 230 disposed on the lower portion thereof and a cap 210 closing the interior thereof that is filled with water. The Mariotte's bottle 200 is disposed on the ground using a support 220, and discharges a predetermined flow rate of water through the second flow rate measuring-and-connecting portion 230 in response to air supplied to the interior thereof through a communication tube 250 extending through the cap 210.

That is, water contained within the Mariotte's bottle 200 is discharged at a constant flow rate through the second flow rate measuring-and-connecting portion 230, from which the water is supplied to the first flow rate measuring-and-connecting portion 130 of the measuring tube 100.

Consequently, the water, which is supplied at a constant flow rate from the Mariotte's bottle 200 to the measuring tube 100 through the flow rate measuring tube 330, flows to the lower portion of the measuring tube 100 under the gravity. Then, the unsaturated porous media within the measuring tube 100 are gradually saturated. At this time, changes in the hydraulic heads in the first hydraulic head observation tube 310 and the second hydraulic head observation tube 320 can be observed depending on the degree of saturation within the measuring tube 100. When the flow of water is stabilized at a saturated state, the hydraulic heads at the first hydraulic head observation tube 310 and the second hydraulic head observation tube 320 are fixed without a change. A hydraulic gradient is obtained by measuring the heat difference Δh at this time. The saturated hydraulic conductivity of the porous media to be measured can be obtained by measuring the flow rate of water supplied to the measuring tube 100 from the Mariotte's bottle 200.

The flow rate of water (Darcian flux) supplied to the measuring tube 100 from the Mariotte's bottle 200 can be obtained using a mass cylinder and a stopwatch or by disposing a pressure sensor within the Mariotte's bottle 200.

The Mariotte's bottle 200 is fixed in a height-adjustable position by a height-adjusting device 225 that presses and fixes the support 220, such that the height of the Mariotte's bottle 200 can be adjusted depending on test conditions.

Alternatively, the apparatus A for measuring hydraulic conductivity according to the present invention can supply a constant flow rate of water to the first flow rate measuring-and-connecting portion 130 of the measuring tube 100 using a metering pump that substitutes the configuration of the Mariotte's bottle 200.

In this manner, the apparatus A for measuring hydraulic conductivity according to the present invention can easily measure the distance between two points, the head difference between two points, the cross-sectional area, and the flow rate that are required when measuring the hydraulic conductivity based on Darcy's Law.

The first hydraulic head side connecting portion 110, the second hydraulic head side connecting portion 120, the first flow rate measuring-and-connecting portion 130, or the like may be damaged in the process of burying the measuring tube 100 in the foundation, depending on the strength of a foundation, the amount of rocks contained in the foundation, or the like.

When any of these components is damaged, it may be difficult to accurately measure the hydraulic conductivity.

Figure 2:
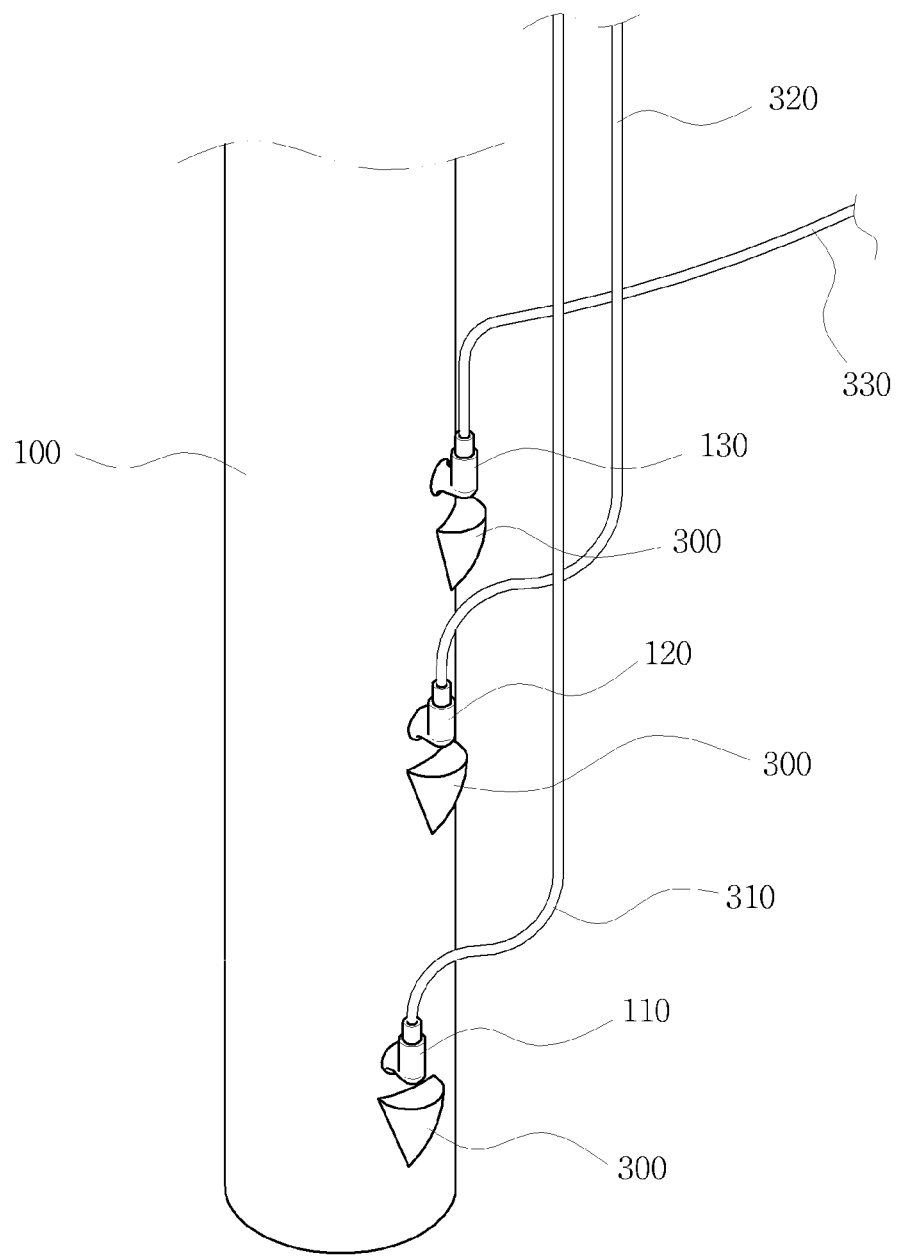
FIG. 2 is a partial enlarged perspective view illustrating protective guides disposed on the measuring tube illustrated in FIG. 1.

For this, a method of preventing these components from being damaged is provided as follows:

FIG. 2 is a partial enlarged perspective view illustrating protective guides disposed on the measuring tube illustrated in FIG. 1.

Referring to FIG. 2, protective guides 300 are disposed on the outer surface of the measuring tube 100.

The protective guides 300 protruding from the measuring tube 100 are configured to shield the corresponding lower portion of the first hydraulic head side connecting portion 110, the second hydraulic head side connecting portion 120, and the first flow rate measuring-and-connecting portion 130. The protective guides 300 protect the first hydraulic head side connecting portion 110, the second hydraulic head side connecting portion 120, and the first flow rate measuring-and-connecting portion 130 while the measuring tube 100 is being buried in the foundation.

The protective guides 300 protrude in a wedge shape to facilitate the burial of the measuring tube 100 while protecting the first hydraulic head side connecting portion 110, the second hydraulic head side connecting portion 120, and the first flow rate measuring-and-connecting portion 130.

In order to accurately measure hydraulic conductivity, the measuring tube 100 must be buried in the foundation in a vertical direction. A configuration for this purpose will be described below.

Figure 3:
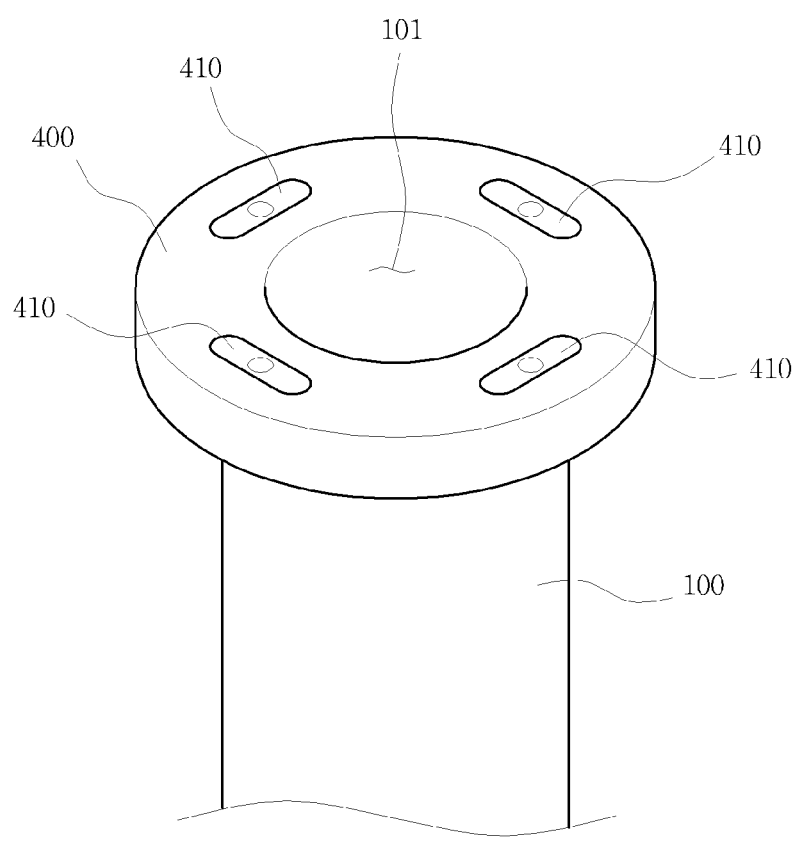
FIG. 3 is a partial enlarged perspective view illustrating gradient measuring devices disposed on the measuring tube illustrated in FIG. 1.

FIG. 3 is a partial enlarged perspective view illustrating gradient measuring devices disposed on the measuring tube illustrated in FIG. 1.

Referring to FIG. 3, gradient measuring devices 410 are disposed on the upper portion of the measuring tube 100.

In addition, the gradient measuring devices 410 may be disposed in the lateral direction and the vertical direction with respect to the plane of the foundation.

With the gradient measuring devices 410, the measuring tube 100 can be buried in the correct direction (the direction vertical to the foundation), and the depth regarding the hydraulic conductivity measured thereby can be accurately determined.

In addition, the gradient measuring devices 410 are disposed on a gradient measuring plate 400 intersecting the longitudinal direction of the measuring tube 100 at right angles.

The gradient measuring plate 400 may be provided for the case in which it is difficult to directly dispose the gradient measuring devices 410 on the upper portion of the measuring tube 100 or the disposition of components including the gradient measuring devices 410 is required at the request of a person skilled in the art.

Figure 4A:
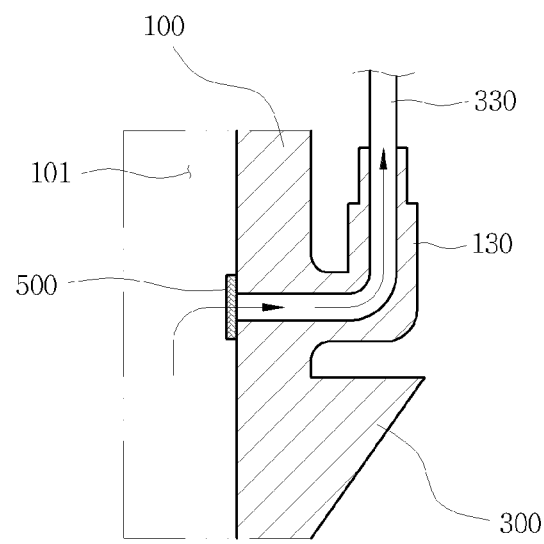
FIGS. 4A and 4B are partial enlarged cross-sectional views illustrating a filter disposed within the measuring tube.
Figure 4B:
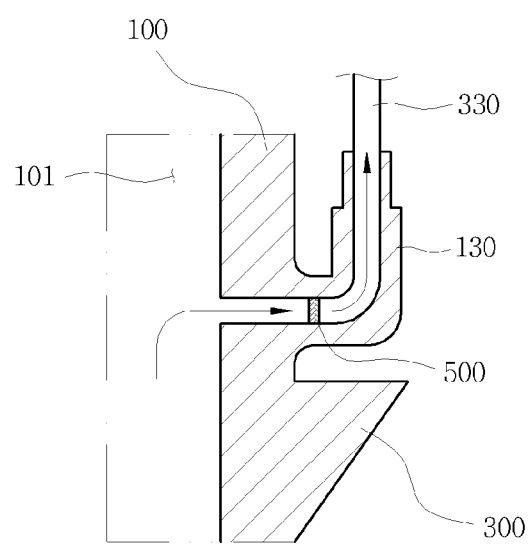

FIGS. 4A and 4B are partial enlarged cross-sectional views illustrating a filter disposed within the measuring tube.

A filter 500 serves to prevent impurities within the measuring tube from entering the first hydraulic head observation tube 310 or the second hydraulic head observation tube 320. The filter may be fixedly disposed, as illustrated in FIGS. 4A and 4B.

According to an embodiment, as illustrated in FIG. 4A, the filter 500 may be disposed on the inner side surface of the measuring tube 100 on which the first flow rate measuring-and-connecting portion 130 is disposed.

According to another embodiment, as illustrated in FIG. 4B, the filter 500 may be disposed within the first flow rate measuring-and-connecting portion 130. The size of the filter 500 and the way how the filter 500 is to be disposed can be variously modified at the request of a person skilled in the art.

Hereinafter, a process of disposing the apparatus A for measuring hydraulic conductivity according to the present invention and a configuration additionally-required therefor will be described.

Figure 5:
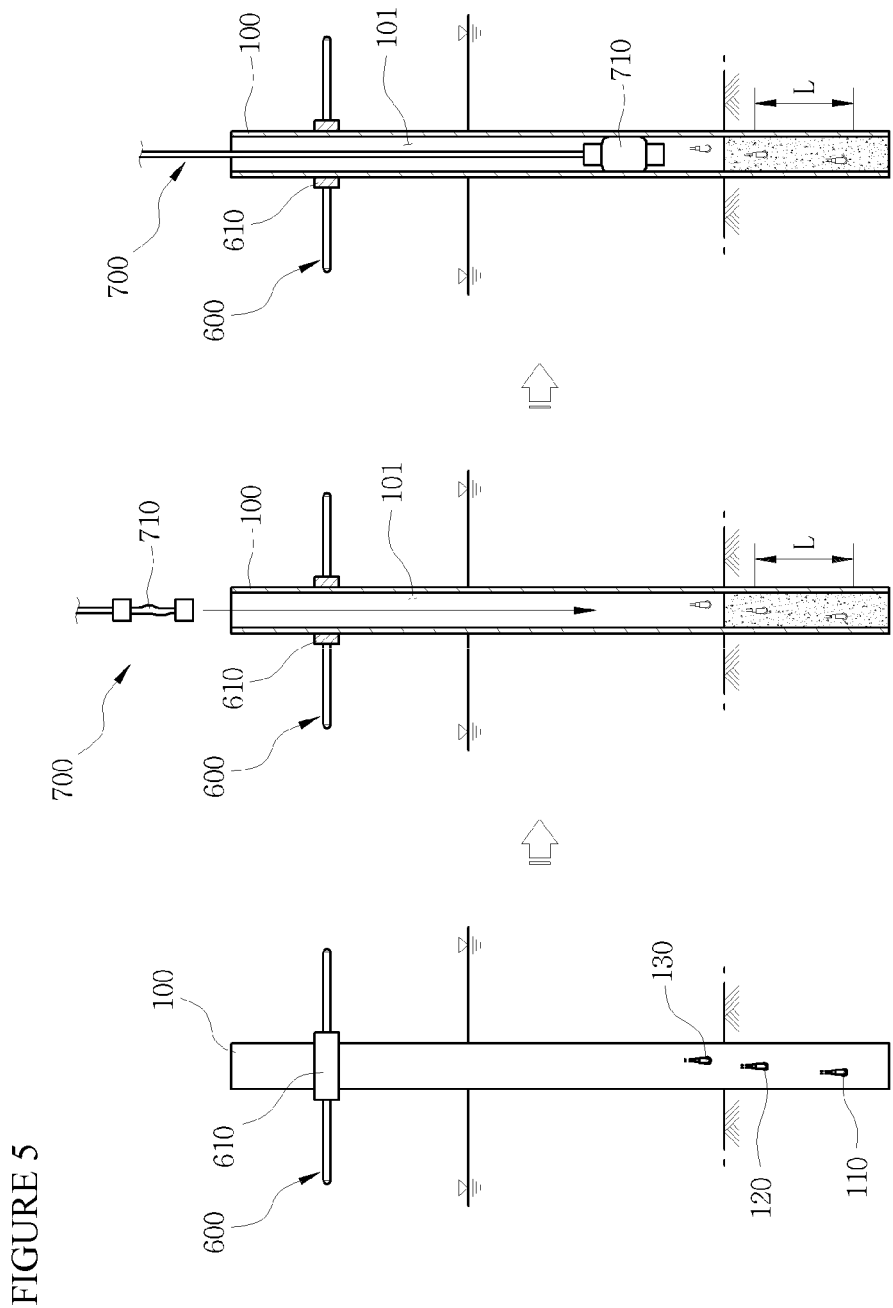
FIG. 5 illustrates a process of disposing the apparatus for measuring hydraulic conductivity as illustrated in FIG. 1.

FIG. 5 illustrates a process of disposing the apparatus for measuring hydraulic conductivity as illustrated in FIG. 1.

Referring to FIG. 5, the measuring tube 100 is buried in a foundation, with a pile-driving support 600 coupled to the upper portion thereof.

The pile-driving support 600 is used to facilitate the burial of the measuring tube 100 in the foundation. For example, when the strength of the foundation is low, a measurer can bury the measuring tube 100 in the foundation by holding the pile-driving support 600 with both hands. For another example, when the strength of the foundation is high, it is possible to bury the measuring tube 100 by beating a body 610 of the pile-driving support 600 using a separate pile driver or a pile-driving device.

In this case, the measuring tube 100 is buried such that the center of the area between the first hydraulic head side connecting portion 110 and the second hydraulic head side connecting portion 120 is positioned at a depth to be measured.

Upon the completion of the burial of the measuring tube 100, a packer 700 is inserted into the hollow portion 101 of the measuring tube 100. Afterwards, a balloon 710 of the packer 700 can be expanded using a hand pump, a gas pressure, or the like. The packer 700 disposed within the hollow portion 101 of the measuring tube 100 is a device that isolates the air layer above the packer 700 from sedimentary layers below the packer 700, thereby guiding water introduced to the sedimentary layers below the packer 700 for flow below the first flow rate measuring-and-connecting portion 130.

Figure 6:
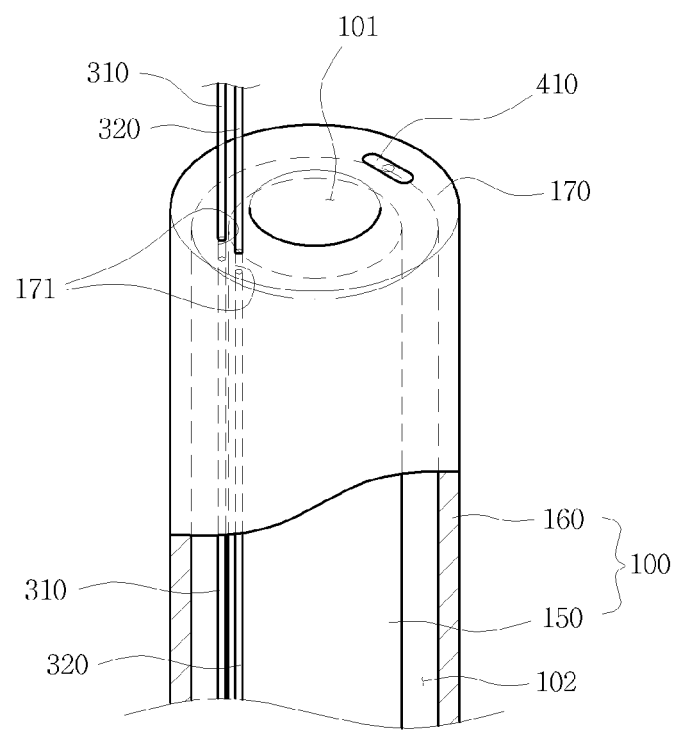
FIGS. 6 and 7 are partially enlarged perspective views illustrating another embodiment of the measuring tube of the apparatus for measuring saturated hydraulic conductivity of unsaturated porous media according to the present invention.
Figure 7:
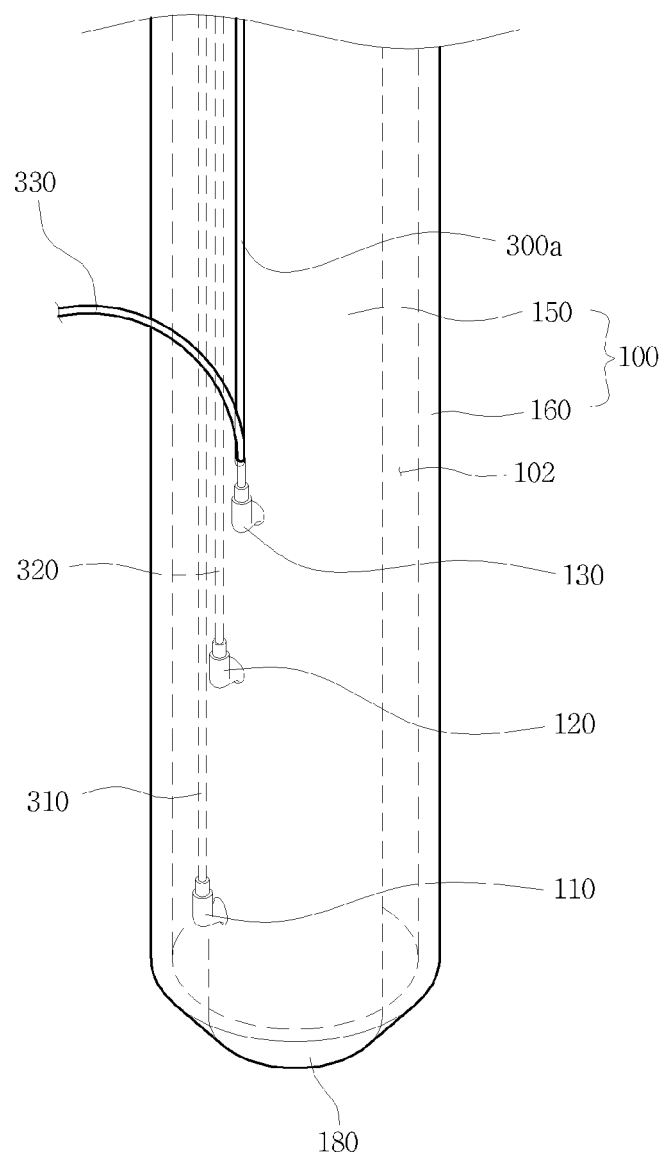

FIGS. 6 and 7 are partially enlarged perspective views illustrating another embodiment of the measuring tube of the apparatus for measuring saturated hydraulic conductivity of unsaturated porous media according to the present invention.

Referring to FIGS. 6 and 7, the measuring tube 100 has a double tube structure including an inner tube 150 and an outer tube 160 spaced apart from each other. An upper connecting portion 170 and a lower connecting portion 180 are disposed on the upper and lower portions of the measuring tube 100 to close a space 102 between the inner tube 150 and the outer tube 160.

In addition, a first hydraulic head side connecting portion 110, a second hydraulic head side connecting portion 120, a flow rate measuring-and-connecting portion 130, a first hydraulic head observation tube 310, a second hydraulic head observation tube 320, and a flow rate measuring tube 330 are disposed between the inner tube 150 and the outer tube 160 of the measuring tube 100.

In addition, the upper connecting portion 170 has fixing holes 171 fixedly holding the first hydraulic head observation tube 310 and the second hydraulic head observation tube 320 such that the first hydraulic head observation tube 310 and the second hydraulic head observation tube 320 are withdrawn upward.

The gradient measuring devices 410 illustrated in FIG. 3 may be disposed on upper connecting portion 170.

In addition, as illustrated in FIG. 7, the outer tube 160 has a withdrawal hole 300a through which the flow rate measuring tube 330 is withdrawn.

Furthermore, the lower connecting portion 180 is tapered downward such that the measuring tube 100 having the double tube structure can be easily buried.

The apparatus for measuring hydraulic conductivity according to the present invention has been described hereinabove. A person skilled in the art will appreciate that various modifications, additions and substitutions are possible from the above-described technical features, without departing from the scope and spirit of the present invention.

It should be understood that the foregoing embodiments have been described in an illustrative manner in all aspects rather than being limitative. The scope of the present invention is defined by the accompanying claims rather than the foregoing detailed description. It should therefore be understood all alterations or modifications derived from the definitions and scopes of the claims and their equivalents fall within the scope of the present invention.

What is claimed is:

1. An apparatus for measuring saturated hydraulic conductivity of unsaturated porous media comprising:
   a measuring tube disposed in a longitudinal direction such that a portion thereof is buried in a foundation, the measuring tube having a hollow portion therein extending in a top-bottom direction to contain a portion of porous media in an unsaturated zone of the foundation, the measuring tube comprising a first hydraulic head side connecting portion and a second hydraulic head side connecting portion on lower portions, the first hydraulic head side connecting portion being spaced apart from the second hydraulic head side connecting portion, and a first flow rate measuring-and-connecting portion disposed above and spaced apart from the first hydraulic head side connecting portion and the second hydraulic head side connecting portion;
   a Mariotte's bottle disposed on a ground, the Mariotte's bottle containing water therein with both ends thereof being closed, the Mariotte's bottle comprising a second flow rate measuring-and-connecting portion connected to the first flow rate measuring-and-connecting portion, wherein the Mariotte's bottle supplies a predetermined flow rate of water to the measuring tube through the second flow rate measuring-and-connecting portion in response to air being supplied to an interior thereof;
   a first hydraulic head observation tube and a second hydraulic head observation tube respectively fixed to the first hydraulic head side connecting portion and the second hydraulic head side connecting portion and extending upward; and
   a flow rate measuring tube connecting the first flow rate measuring-and-connecting portion and the second flow rate measuring-and-connecting portion.

2. The apparatus according to claim 1, further comprising protective guides on an outer surface of the measuring tube respectively protruding from below the first hydraulic head side connecting portion, the second hydraulic head side connecting portion, and the first flow rate measuring-and-connecting portion to protect the first hydraulic head side connecting portion, the second hydraulic head side connecting portion, and the first flow rate measuring-and-connecting portion while the measuring tube is being buried in the foundation.

3. The apparatus according to claim 2, wherein the protective guides protrude in a wedge shape.

4. The apparatus according to claim 1, further comprising at least one gradient measuring device on an upper portion of the measuring tube.

5. The apparatus according to claim 1, further comprising:
   a gradient measuring plate on an upper portion of the measuring tube; and
   at least one gradient measuring device fixedly disposed on an upper surface of the gradient measuring plate.

6. The apparatus according to claim 1, further comprising a filter fixedly disposed on at least one of an inner side surface of the measuring tube on which the first flow rate measuring-and-connecting portion is disposed and or an interior of the first flow rate measuring-and-connecting portion.

7. The apparatus according to claim 1, further comprising a packer disposed within the hollow portion of the measuring tube to selectively isolate an upper portion and a lower portion of the hollow portion from each other.

8. An apparatus for measuring saturated hydraulic conductivity of unsaturated porous media comprising:
   a measuring tube comprising an inner tube and an outer tube forming a double tube structure, lower portions of the inner tube and the outer tube being connected to each other and forming a lower connecting portion, the measuring tube being disposed in a longitudinal direction such that a portion thereof is buried in a foundation, the measuring tube having a hollow portion therein extending in a top-bottom direction to contain a portion of porous media in an unsaturated zone of the foundation, the measuring tube further comprising a first hydraulic head side connecting portion and a second hydraulic head side connecting portion on lower portions between the inner tube and the outer tube, the first hydraulic head side connecting portion being spaced apart from the second hydraulic head side connecting portion, and a first flow rate measuring-and-connecting portion disposed above and spaced apart from the first hydraulic head side connecting portion and the second hydraulic head side connecting portion;
   a Mariotte's bottle disposed on a ground, the Mariotte's bottle containing water therein with both ends thereof being closed, the Mariotte's bottle comprising a second flow rate measuring-and-connecting portion connected to the first flow rate measuring-and-connecting portion, wherein the Mariotte's bottle supplies a predetermined flow rate of water to the measuring tube through the second flow rate measuring-and-connecting portion in response to air being supplied to an interior thereof;
   a first hydraulic head observation tube and a second hydraulic head observation tube respectively fixed to the first hydraulic head side connecting portion and the second hydraulic head side connecting portion and extending upward; and
   a flow rate measuring tube connecting the first flow rate measuring-and-connecting portion and the second flow rate measuring-and-connecting portion.

9. The apparatus according to claim 8, wherein
   the upper connecting portion is disposed on an upper portion of the measuring tube to connect the upper portions of the inner tube and the outer tub, and
   the upper connecting portion has fixing holes fixedly holding the first hydraulic head observation tube and the second hydraulic head observation tube such that the first hydraulic head observation tube and the second hydraulic head observation tube are withdrawn upward.

10. The apparatus according to claim 9, further comprising at least one gradient measuring device on the upper connecting portion.

11. The apparatus according to claim 8, wherein the outer tube has a withdrawal hole through which the flow rate measuring tube is withdrawn.

12. The apparatus according to claim 8, further comprising a filter fixedly disposed on at least one of an inner side surface of the measuring tube on which the first flow rate measuring-and-connecting portion is disposed or an interior of the first flow rate measuring-and-connecting portion.

13. The apparatus according to claim 8, further comprising a packer disposed within the hollow portion of the measuring tube to selectively isolate an upper portion and a lower portion of the hollow portion from each other.

\* \* \* \* \*